US007037583B2

(12) United States Patent
Furman et al.

(10) Patent No.: US 7,037,583 B2
(45) Date of Patent: May 2, 2006

(54) FUNCTIONALIZED ZIRCONIUM OXIDE PARTICLES

(75) Inventors: Benjamin R. Furman, San Antonio, TX (US); Stephen T. Wellinghoff, San Antonio, TX (US); Henry R. Rawls, San Antonio, TX (US); Hong Dixon, Helotes, TX (US); Barry K. Norling, San Antonio, TX (US)

(73) Assignees: Southwest Research Institute, San Antonio, TX (US); Board of Regents, The University of Texas Systems, Austin, TX (US)

( * ) Notice: Subject to any disclaimer, the term of this patent is extended or adjusted under 35 U.S.C. 154(b) by 510 days.

(21) Appl. No.: 09/726,769

(22) Filed: Nov. 29, 2000

(65) Prior Publication Data

US 2002/0013382 A1 Jan. 31, 2002

Related U.S. Application Data

(63) Continuation-in-part of application No. 09/314,350, filed on May 19, 1999, now Pat. No. 6,194,481.

(51) Int. Cl.
*B32B 5/16* (2006.01)
(52) U.S. Cl. ...................................... 428/403; 428/407
(58) Field of Classification Search ............... 428/403, 428/407, 323, 328, 327
See application file for complete search history.

(56) References Cited

U.S. PATENT DOCUMENTS

| 4,201,856 | A |   | 5/1980  | Jackson, Jr.    |
|-----------|---|---|---------|-----------------|
| 4,215,033 | A |   | 7/1980  | Bowen           |
| 4,539,048 | A |   | 9/1985  | Cohen           |
| RE32,073  | E |   | 1/1986  | Randklev        |
| 4,588,756 | A |   | 5/1986  | Bowen           |
| 4,623,738 | A |   | 11/1986 | Sugerman et al. |
| 4,659,751 | A |   | 4/1987  | Bowen           |
| 4,663,147 | A |   | 5/1987  | DePrince        |
| 4,753,652 | A |   | 6/1988  | Langer et al.   |
| 4,873,064 | A | * | 10/1989 | Kato ............................ 423/85 |
| 4,914,221 | A |   | 4/1990  | Winkler et al.  |
| 4,964,911 | A |   | 10/1990 | Ibsen et al.    |
| 4,978,640 | A |   | 12/1990 | Kelly           |
| 5,024,850 | A |   | 6/1991  | Broer et al.    |
| 5,030,608 | A |   | 7/1991  | Schubert et al. |
| 5,057,018 | A |   | 10/1991 | Bowen           |
| 5,064,877 | A |   | 11/1991 | Nass et al.     |
| 5,073,294 | A |   | 12/1991 | Shannon et al.  |
| 5,202,053 | A |   | 4/1993  | Shannon         |
| 5,276,068 | A |   | 1/1994  | Waknine         |
| 5,308,886 | A |   | 5/1994  | Masuhara et al. |
| 5,328,947 | A |   | 7/1994  | Taguchi et al.  |
| 5,334,625 | A |   | 8/1994  | Ibsen et al.    |
| 5,372,796 | A |   | 12/1994 | Wellinghoff     |
| 5,401,528 | A |   | 3/1995  | Schmidt         |
| 5,472,491 | A | * | 12/1995 | Duschek et al.  |
| 5,472,797 | A |   | 12/1995 | Yajima et al.   |
| 5,486,548 | A |   | 1/1996  | Podszun et al.  |
| 5,502,087 | A |   | 3/1996  | Tateosian et al.|
| 5,519,088 | A | * | 5/1996  | Itoh et al.     |
| 5,556,931 | A |   | 9/1996  | Imura et al.    |
| 5,563,230 | A |   | 10/1996 | Hsu et al.      |
| 5,622,648 | A |   | 4/1997  | Parri           |
| 5,624,976 | A |   | 4/1997  | Klee et al.     |
| 5,654,471 | A |   | 8/1997  | Zahn et al.     |
| 5,663,214 | A |   | 9/1997  | Okada           |
| 5,670,583 | A |   | 9/1997  | Wellinghoff     |
| 5,695,681 | A |   | 12/1997 | Siemensmeyer et al. |
| 5,710,194 | A | * | 1/1998  | Hammesfahr et al. |
| 5,720,805 | A |   | 2/1998  | Wellinghoff et al. |
| 5,730,601 | A |   | 3/1998  | Bowman et al.   |
| 5,804,097 | A |   | 9/1998  | Delavier et al. |
| 5,808,108 | A |   | 9/1998  | Chappelow et al.|
| 5,833,880 | A |   | 11/1998 | Siemensmeyer et al. |
| 5,834,532 | A |   | 11/1998 | Yamamoto et al. |
| 5,852,248 | A |   | 12/1998 | Chadwick        |
| 5,859,089 | A |   | 1/1999  | Qian            |
| 5,865,623 | A |   | 2/1999  | Suh             |
| 5,871,665 | A |   | 2/1999  | Coates et al.   |
| 5,886,064 | A |   | 3/1999  | Rheinberger et al. |
| 5,897,885 | A |   | 4/1999  | Petticrew       |
| 5,900,315 | A | * | 5/1999  | Little          |
| 5,910,273 | A |   | 6/1999  | Thiel et al.    |
| 5,911,911 | A |   | 6/1999  | Keller et al.   |
| 5,955,514 | A |   | 9/1999  | Huang et al.    |
| 5,989,461 | A |   | 11/1999 | Coates et al.   |
| 5,998,499 | A |   | 12/1999 | Klee et al.     |
| 6,020,412 | A | * | 2/2000  | Muschelewicz et al. .... 524/296 |
| 6,022,404 | A |   | 2/2000  | Ettlinger et al. |
| 6,027,816 | A |   | 2/2000  | Ono et al.      |
| 6,031,015 | A |   | 2/2000  | Ritter et al.   |

(Continued)

FOREIGN PATENT DOCUMENTS

CA      2181507        1/1997

(Continued)

OTHER PUBLICATIONS

Michael Dewar et al., "*Factors Influencing the Stabilities of Nematric Liquid Crystals*", J. Am. Chem. Soc., (1975), 97(23), 6658-6666.

(Continued)

*Primary Examiner*—H. T Le
(74) *Attorney, Agent, or Firm*—Paula D. Morris; The Morris Law Firm, P.C.

(57) ABSTRACT

Metal oxide nanoparticles having at least some surface acid sites functionalized with an adhesion promoter and at least some surface acid sites functionalized with a coupling agent. The nanoparticles are useful in forming composites comprising photopolymerizable matrix monomers, and are primarily suitable for dental and medical restoration. In a preferred embodiment, the metal oxide comprises zirconium, and the coupling agent is a zirconate.

108 Claims, No Drawings

U.S. PATENT DOCUMENTS

| | | | |
|---|---|---|---|
| 6,060,042 | A | 5/2000 | Schuhmacher et al. |
| 6,087,816 | A | 7/2000 | Volk |
| 6,090,308 | A | 7/2000 | Coates et al. |
| 6,117,920 | A | 9/2000 | Jolliffe et al. |
| 6,132,874 | A * | 10/2000 | Fischer et al. |
| 6,136,225 | A | 10/2000 | Meyer et al. |
| 6,144,428 | A | 11/2000 | Schadt et al. |
| 6,194,481 | B1 * | 2/2001 | Furman et al. ............... 522/77 |
| 6,204,302 | B1 | 3/2001 | Rawls |
| 6,217,792 | B1 | 4/2001 | Parri et al. |
| 6,217,955 | B1 | 4/2001 | Coates et al. |
| 6,258,974 | B1 | 7/2001 | Wellinghoff |
| 6,291,035 | B1 | 9/2001 | Verrall et al. |
| 6,303,050 | B1 | 10/2001 | Dannenhauer et al. |
| 6,306,926 | B1 * | 10/2001 | Bretscher et al. |
| 6,335,462 | B1 | 1/2002 | Etzbach |
| 6,350,519 | B1 * | 2/2002 | Devonport |
| 6,376,590 | B1 * | 4/2002 | Kolb et al. |
| 6,387,981 | B1 * | 5/2002 | Zhang et al. ............... 523/117 |
| 6,410,765 | B1 | 6/2002 | Wellinghoff |
| 6,414,092 | B1 | 7/2002 | Coates et al. |
| 6,417,244 | B1 | 7/2002 | Wellinghoff |
| 6,593,395 | B1 * | 7/2003 | Angeletakis et al. ........ 523/115 |
| 6,649,230 | B1 | 11/2003 | Seiberle et al. |
| 6,656,990 | B1 * | 12/2003 | Shustack et al. ............ 524/430 |
| 6,695,617 | B1 | 2/2004 | Wellinghoff |
| 6,696,585 | B1 | 2/2004 | Wellinghoff |
| 6,699,405 | B1 | 3/2004 | Prechtl et al. |
| 6,743,936 | B1 | 6/2004 | Wellinghoff |
| 2002/0013382 | A1 | 1/2002 | Furman |
| 2002/0036285 | A1 | 3/2002 | Prechtl et al. |
| 2002/0177727 | A1 | 11/2002 | Wellinghoff |
| 2003/0036609 | A1 | 2/2003 | Wellinghoff |
| 2003/0055280 | A1 | 3/2003 | Wellinghoff |
| 2003/0125435 | A1 | 7/2003 | Norling |
| 2003/0168633 | A1 | 9/2003 | Wellinghoff |
| 2004/0144954 | A1 | 7/2004 | Wellinghoff |
| 2004/0199004 | A1 | 10/2004 | Wellinghoff |

FOREIGN PATENT DOCUMENTS

| | | |
|---|---|---|
| DE | WO 94/16183 | 10/1992 |
| DE | 0722992 A1 | 7/1996 |
| EP | 015987 B1 | 10/1985 |
| EP | 0159887 A2 | 10/1985 |
| EP | 0 242 278 A2 | 10/1987 |
| EP | 0 754675 A2 | 7/1996 |
| EP | 0722992 A1 | 7/1996 |
| EP | 0 869 112 A1 | 3/1998 |
| EP | 1142863 A2 | 10/2001 |
| GB | 2 297 549 A | 7/1996 |
| JP | H 3-344860 | 12/1991 |
| JP | 5178794 | 7/1993 |
| WO | WO 7901040 | 11/1979 |
| WO | WO 92/16183 | 10/1992 |
| WO | WO 93/22397 | 11/1993 |
| WO | WO 94/16129 | 7/1994 |
| WO | WO 9416129 | 7/1994 |
| WO | WO 9424052 | 10/1994 |
| WO | WO 9714674 | 4/1997 |
| WO | WO 98/13008 | 4/1998 |
| WO | WO 9823580 | 4/1998 |
| WO | WO 99/17716 | 4/1999 |
| WO | WO 02/070543 A2 | 9/2002 |

OTHER PUBLICATIONS

Y. Wei, "Synthesis of New Organic-Inorganic Hybrid Glasses", Chem. Mater. (1990), 2(4), 337-339.

W. Wedler et al., "Vitrification in Low-molecular-weight Mesogenic Compounds", J. Mater Chem., (1991), 1(3), 347-356.

Sukmin Lee et al., "Phase Behavior of Liquid Crystalline Polymer/Model Compound Mixtures: Theory and Experiment", Macromolecules, (1994), 27, 3955-3962.

R. A. M. Hikmet et al., "Effect of the Orientation of the Ester Bonds on the Properties of Three Isomeric Liquid Crystal Diacrylates before and after Polymerization", Macromolecules (1995), 28, 3313-3327.

H. Schmidt et al., "Organically modified ceramics and their applications", Journal of Non-Crystalline Solids, 1990, 121, pp. 428-435.

Mark Ellsworth et al., "Mutually intepenetrating inorganic-organic networks. New Routes into nonshrinking sol-gel composite materials", J. Am. Chem. Soc., 1991,113, 2756-2758.

Christine Landry et al., "In situ polymerization of tetraethoxysilane in poly(mtehyl methacrylate): morphology and dynamic mechanical properties", Polymer, 1992, vol. 33, No. 7, pp. 1486-1495.

Stephen Wellinghoff et al., "Tantalum oxide-polymer composites", The International Symposium on Advances in Sol-Gel Processing and Applications, Edited by Y.A. Attia, Plenum Press, pp. 141-154, 1994.

"Nanostructured Materials: A Technical-Market Analysis", Mindy N. Rittner, Business Communications Co., Inc.; Fine, Ultrafine and Nano Powders '98'.

Schmidt, et al., New Liquid Crystalline di-and tetra-acrylates for network formation, Liquid Crystals; 2001, vol. 28, No. 11, 1611-1621.

Choi, Rheological studies on sterically stabilized model dispersions of uniform colloidal spheres. II. Steady-shear viscosity, J. Colloid Interface Science., Sep. 1986, pp. 101-113, vol. 113(1), Academic Press, Inc.

Condon, Reduction of composite contraction stress through non-bonded microfiller particles, Dental Materials, Jul. 1998, pp. 256-260, vol. 14.

Hellwig, Influence of an incremental application technique on the polymerization of two light-activated dental composite filling materials, Dtsch. Zahnaerzil Z., 1991, pp. 270-273, vol. 46.

Hikmet, Anisotropic polymerization shrinkage behavior of liquid-crystalline diacrylates, Polymer, 1992, pp. 89-95, vol. 33(1), Butterworth-Heinemann Ltd.

Node, Hard Acid and Soft Nucleophile System. 2. Demethylation of Methyl Ethers of Alcohol and Phenol with an Aluminum Halide-Thiol System, J. Org. Chem., 1980, pp. 4275-4277, vol. 45, The American Chemical Society.

Liu, Constant-volume polymerization of composites by addition of ammonia-modified montmorillonite, American Journal of Dentistry, Apr. 1990, pp. 44-50, vol. 3(2).

Millich, Elements of light-cured epoxy based dental polymer systems, J. Dent. Res., Apr. 1998, pp. 603-608, vol. 77(4).

Rawls et al, Low Shrinkage resins from liquid crystal diacrylate monomers, ACS Polymer Preprints, Sep. 1997, pp. 167-168, vol. 38(2).

Stansbury et al, Cyclopolymerizable Monomers for use in dental resin composites, J. Dent. Res., Mar. 1990, pp. 844-848, vol. 69(3).

Uno et al, Marginal adaptation of a restorative resin polymerized at reduced rate, Scand. J. Dent. Res., 1991, pp. 440-444, vol. 99(5).

Holmberg, Ester Synthesis with Dicyclohexycarbodiimide Improved by Acid Catalysts, Acta Chemica Scandinavica, 1979, pp. 410-412, vol. B 33.

Nakamura, Characterization of Epitaxially Grown ZnS : Mn Films on a GaAs(100) Substrate prepared by the Hot-wall Epitaxy Technique, J. Mater. Chem., 1991, pp. 357-359, vol. 1(3).

Schultz, Polymerization and Viscoelastic Behavior of Networks from a Dual-Curing, Liquid Crystalline Monomer, J. Polym. Phys., 1999, pp. 1183-1190, vol. 37, John Wiley & Sons, Inc.

Griffin, Mesogenic Polymers, III. Thermal Properties and Synthesis of Three Homologous Series of Thermotropic Liquid Crystalline "Backbone" Polyesters, Journal of Polymer Science: Polymer Physics Edition, 1981, pp. 951-969, vol. 19, John Wiley & Sons, Inc.

Hutchins, Aqueous Polar Aprotic Solvents. Efficient Sources of Nucleophilic Oxygen, J. Org. Chem. 1983, pp. 1360-1362, vol. 48, The American Chemical Society.

Kornblum, Displacement of the Nitro Group of Substituted Nitrobenzenes—a Synthetically Useful Process, J.Org. Chem., 1976, pp. 1560-1564, vol. 41, The American Chemical Society.

Clark, X-Ray Scattering Study of Smectic Ordering in a Silica Aerogel, Physical Review Letters, Nov. 22, 1993, pp. 3505-3508, vol. 71, No. 21, The American Chemical Society.

Broer, In-Situ photopolymerization of oriented liquid-crystalline acrylates, 4 Influence of a lateral methyl substituent on monomer and oriented polymer network properties of a mesogenic diacrylate, Makromol. Chem. 1989, pp. 3201-3215, vol. 190, Huthig & Wepf Verlag Basel, Heidelberg, New York.

Barclay, Liquid Crystalline and Rigid-rod Networks, Prog. Polym. Sci., 1993, pp. 899-945, vol. 18(5), Pergamon Press Ltd.

Liquid Crystalline Polymers to Mining Applications, Encyclopedia of Polymer Science and Engineering, 1987, pp. 1-61, vol. 9, John Wiley & Sons, New York.

Galli, Thermotropic poly(ester-B-sulfide)s—A new polymer series containing the p-phenylene di(p-oxybenzoate) unit, Polymer Bulletin, 1989, pp. 563-569, vol. 21, Springer-Verlag.

Meek, Inertness of Tetrachlorofulvenes in the Diels-Alder Reaction, J. Org. Chem., Jan. 9, 1958, pp. 1708-1710, vol. 22 (12), The American Chemical Society.

Suzuki et al, Preparation of poly(dimethylsiloxane) macromonomers by the initiator method: 2. Polymerization mechanism, Polymer, 1989, pp. 333-337, vol. 30(2), Butterworth & Co. (Publishers) Ltd.

Kochan et al, Solid Freeform Manufacturing—Assessments and Improvements at the Entire Process Chain, Proceedings of the Seventh International Conference on Rapid Prototyping, Mar. 31-Apr. 3, 1997, pp. 203-214, 94RA021.

Norling et al, Cure shrinkage of experimental LC monomer based composite resins, Abstract, American Association for Dental Research meeting, 2001, Chicago, IL.

Mogri et al, Thermomechanical of liquid crystalline monomer in dental composites, Abstract, American Association for Dental Research meeting, 2001, Chicago, IL.

Dowell et al, The Effect of Silanation on Polymerization and Dynamic Mechanical Behavior of a homogenous nanofilled resin, Abstract, American Association for Dental Research meeting, 2001, Chicago, IL.

Logan et al, Effect of Silanation on Mechanical Properties of Homogeneous Nanofilled resins, Abstract, American Association for Dental Research meeting, 2001, Chicago, IL.

Norling et al, Synthesis of a new low shrinkage liquid crystal monomer, Abstract, American Association for Dental Research meeting, 2000, Washington, D.C.

Furman et al, A Radiopaque Zirconia Microfiller for Translucent Composite Restoratives, Abstract, American Association for Dental Research meeting, 2000, Washington, D.C.

Norling et al, Polymerizable nematic liquid crystal monomers for reduced shrinkage restorative resins, Proc. 17th Southern Biomed. Eng. Conf., 1998, p. 120.

Geng, Targeted Drug Release by a Novel Polymeric Device Based on EVA (Ethylene Vinyl Acetate) For Periodontal Condition, (Abstract).

Boland et al, Cell Survival and Cytokine Expression by Dental Cells Treated with a Liquid Crystal Resin Monomer, J. Dent. Res., 2001, pp. 151 (Abstract 928), vol. 80.

Wang, Rheological Properties of Dental Composites, (Abstract).

Wellinghoff et al, Reduced Shrinkage dimethacrylate liquid crystal resins, J. Den. Res. 1997, pp. 279 (Abstract 2127), vol. 76.

Norling et al, Cure shrinkage of composite resins and an experimental LC monomer, J. Dent. Res., 1999, pp. 233 (Abstract 1020), vol. 78.

Panyayong, Effects of Corn-Starched & Primer Additions on Mechanical Properties of Provisional Dental Resin, (Abstract).

* cited by examiner ically strong and stable.
FUNCTIONALIZED ZIRCONIUM OXIDE PARTICLES The U.S. government has certain rights in this invention pursuant to grant number NIDCR 1 P01 DE11688.

FIELD OF THE INVENTION

The present invention relates to metal oxide particles comprising surface hydroxyl groups which are functionalized for a variety of reasons. The invention maximizes the fraction of hydroxyl groups functionalized by reacting the hydroxyl groups with two or more different functionalities comprising different steric hindrances. Some hydroxyl groups, called "reactive groups" are accessible to both functionalities. Hydroxyl groups that are not accessible to the functionalities having greater steric hindrance are accessible to functionalities with less steric hindrance. In a more preferred embodiment, the metal oxide particles are zirconium oxide particles, the mobile adhesion promoters are silanes, and the organofunctional coupling agents are zirconates. The composites primarily are suitable for dental and medical restoration; however, optical resins for use in high refractive index applications such as eyeglasses, resins for advanced prototyping, and adhesive applications also are possible.

BACKGROUND OF THE INVENTION

Colloidal fumed silica nanoparticles currently are used as fillers in "microfilled" composite dental restorative resins. These particles can increase the hardness and wear resistance of photocured matrix polymers; however, the particles are not radiopaque and cannot be homogeneously dispersed within the matrix resin because of interparticle associations. The resulting coagulation leads to a substantial increase in viscosity and a consequent decrease in composite workability. This places a severe limitation on the practical filler loading in "microfilled" composites.

The loading problem can be partially offset by incorporating prepolymerized organic fillers into the resin in which a relatively high level of colloidal silica is incorporated into highly crosslinked polymeric granules. The workability of the composite resins containing these fillers is maintained, and the cure shrinkage is somewhat reduced. However, the fillers also yield failure prone interfaces and cause a high degree of light scattering, thereby limiting the depth of cure.

Photocurable dental repair materials are needed which are transparent or translucent, radioopaque, have good workability, and have good mechanical strength and stability. The use of metal oxides as fillers in such materials results in transparent or translucent, radioopaque materials. However, the hydroxyl groups that tend to form at the surface of metal oxide particles in "protic" environments tend to make the surface of the particles hydrophilic. As a result, the metal oxide particles have difficulty being wetted or adhered to by relatively hydrophobic matrix monomers, such as acrylic monomers, which are non-polar or only weakly polar in nature.

Methods are need to functionalize as many of these hydroxyl groups as possible in order to render the surface of metal oxide particles more hydrophobic.

SUMMARY OF THE INVENTION

The present invention provides functionalized metal oxide particles comprising a surface comprising a total quantity of hydroxyl groups comprising a complexed fraction and an uncomplexed fraction, the complexed fraction being effective to produce a coagulation point of about one minute or more after removal of a solvent from a mixture comprising said metal oxide particles and a matrix resin.

DETAILED DESCRIPTION OF THE INVENTION

The present invention relates to metal oxide particles comprising surface hydroxyl groups functionalized for a variety of reasons. Two primary reasons are (a) to render the surface polymerizable with a matrix resin, and (b) to render the surface hydrophobic. The present invention maximizes the "complexed fraction" of the total quantity of surface hydroxyl groups, or the fraction of the total quantity of surface hydroxyl groups that are functionalized. The present invention recognizes that the surface hydroxyl groups on metal oxide particles have different "accessibilities," and therefore have different reactivities towards groups with different steric hindrances.

For purposes of the present invention, functionalities with a "low steric hindrance" are defined as functionalities having a formula weight of less than about 250 grams/mole, preferably about 150 grams/mole or less. Functionalities with a "high steric hindrances" are defined as functionalities having a formula weight of about 250 grams/mole or more, preferably of about 300 g/mole or more.

Hydroxyl groups that are accessible to and complex with functionalities having a variety of both high steric hindrances and low steric hindrances are herein defined as "reactive groups." Hydroxyl groups that are accessible only to functionalities having low steric hindrance are herein defined as "less reactive groups."

Suitable agents with high steric hindrance include, but are not necessarily limited to organofunctional coupling agents, defined in more detail below. Suitable agents with less steric hindrance include, but are not necessarily limited to adhesion promoters, preferably mobile adhesion promoters, defined in more detail below. A preferred embodiment of the invention functionalizes the surface hydroxyl groups of metal oxide particles with a combination of both organofunctional coupling agents and adhesion promoters. Using functionalities with differing steric hindrances maximizes the fraction of the total quantity of the surface hydroxyl groups functionalized, rendering the surface of the metal oxide particle less protic and more hydrophobic. In a preferred embodiment, substantially all of the hydroxyl groups are functionalized.

In a preferred embodiment, the metal oxide particles are zirconium oxide particles, the mobile adhesion promoters are silanes, and the organofunctional coupling agents are zirconates. The composites primarily are suitable for dental and medical restoration; however, optical resins for use in high refractive index applications such as eyeglasses, resins for advanced prototyping, and adhesive applications also are possible.

The invention encompasses the functionalized metal oxide particles alone, a mixture of the metal oxide particles combined with a resin comprising matrix monomers copolymerizable with functionalities on the metal oxide clusters, and the composite formed when the resin is copolymerized with the polymerizable functionalities on the surface of the metal oxide clusters. The mixture has good workability, and forms a composite which is mechanically strong and stable. Substantially any "metal" capable of forming an amphoteric metal oxide may be used to form the metal oxide particles.

Suitable metallic elements include, but are not necessarily limited to niobium, indium, titanium, zinc, zirconium, tin, cerium, hafnium, tantalum, tungsten, and bismuth. Also suitable in place of the metal in the oxide is the semi-metallic compound, silicon. As used herein, unless otherwise indicated, the term "metal oxide" is defined to include silicon, and the word "metal," when used to refer to the metal oxide is intended to also refer to silicon.

The metal oxides may be made of a single metal, or may be a combination of metals, alone or combined with other impurities or "alloying" elements, including, but not necessarily limited to aluminum, phosphorus, gallium, germanium, barium, strontium, yttrium, antimony, and cesium. Binary and tertiary compounds may be more easy to silanate, and may be produced by mixing precursors containing different metal or semi-metal groups. Preferred metal oxide particles comprise zirconium oxide. Alternately, it may be preferable to use zirconium silicate particles (commonly known as "zircon"), as zircon is easier to silanate than zirconium.

The metal oxide nanoparticles may be prepared using any known methods, such as "sol-gel" techniques, direct hydrolysis of metal alkoxides by water addition, forced hydrolysis of relatively low-cost metal salts, or non-hydrolytic reactions of metal alkoxides with metal halide salts. Examples of such procedures are shown in the following references, each of which is incorporated herein by reference: W. Stöber and A. Fink, J. of Colloid and Interface Science, v. 26, 62–69 (1968); M. Z.-C. Hu, M. T. Harris, and C. H. Byers, J. of Colloid and Interface Science, v. 198, 87–99 (1988); M. Ocaña and E. Matijević, J. of Materials Research, v. 5(5), 1083–1091 (1990); L. Lerot, F. LeGrand, P. de Bruycker, J. of Materials Science, v. 26, 2353–2358 (1991); H. Kumazawa, Y. Hori, and E. Sada, The Chemical Eng'g. Journal, v. 51, 129–133 (1993); S. K. Saha and P. Pramanik, J. of Non-Crystalline Solids, v. 159, 31–37 (1993); M. Andrianainarivelo, R. Corriu, D. Leclercq, P. H. Mutin, and A. Vioux, J. of Materials Chemistry, v. 6(10), 1665–1671 (1996); F. Garbassi, L. Balducci, R. Ungarelli, J. of Non-Crystalline Solids, v. 223, 190–199 (1998); J. Spatz, S. Mössmer, M. Mo[umlaut]ller, M. Kocher, D. Neher, and G. Wegner, Advanced Materials, v. 10(6), 473–475 (1998); R. F. de Farias, and C. Airoldi, J. of Colloid and Interface Science, v. 220, 255–259 (1999); T. J. Trentler, T. E. Denler, J. F. Bertone, A. Agrawal, and V. L. Colvin, J. of the Am. Chemical Soc., v. 121, 1613–1614 (1999); Z. Zhan and H. C. Zheng, J. of Non-Crystalline Solids, v. 243, 26–38 (1999); M. Lade, H. Mays, J. Schmidt, R. Willumeit, and R. Schomäcker, Colloids and Surfaces A: Physiochemical and Eng'g Aspects, v. 163, 3–15 (2000); and the procedure described in "Sol-gel processing with inorganic metal salt precursors," authored by "Michael" Zhong Cheng Hu, licensable via Oak Ridge National Laboratory under ORNL control number ERID 0456.

A preferred method of forming the metal oxide nanoparticles is water hydrolysis of corresponding metal alkoxides, preferably normal metal alkoxides having from about 1 to about 4 carbon atoms per hydrolyzable group. Where the metal used is zirconium, a preferred zirconium alkoxide for use in this procedure is zirconium propoxide. Although the following description is couched in terms of preparing zirconium oxide particles, the description applies equally to the preparation of other metal oxide nanoparticles.

If desired, the cluster synthesis may be enhanced using a suitable acid, preferably formic acid, as described in U.S. Pat. No. 5,372,796 to Wellinghoff, incorporated herein by reference. Hydrolysis without using formic acid enhancement preferably takes place in the presence of excess alcohol as a diluent, preferably ethanol or propanol, most preferably n-propanol, in the presence of an inert gas, preferably nitrogen gas. Small droplets of water for hydrolyzing the zirconium alkoxide preferably are progressively added to the solution while stirring. The water droplets also preferably are diluted to a concentration of from about 1% (w/w) to about 3% (w/w) in a lower alcohol having from about 1 to about 3 carbon atoms, preferably propanol. In order to fully hydrolyze the zirconium alkoxide, the amount of water added must be twice the molar amount of the zirconium alkoxide unless the hydrolysis is enhanced using formic acid. During the addition of the water droplets, the solution is stirred vigorously. Typically, the addition of acid to produce a pH of about 3 is sufficient to form an adequate dispersion of zirconia clusters. Substantially any acid having a pH of less than about 3 may be used for this purpose, suitable acids including but not necessarily limited to nitric acid, hydrochloric acid, sulfuric acid, and the like. The chemical stoichiometry is as follows:

$$Zr(OPr)_4 + 2H_2O \rightarrow ZrO_2 + 4PrOH$$

In a preferred embodiment, a suitable organic acid is used to increase the rate of hydrolysis and to increase the amount of positive surface charge on the resulting zirconia clusters while producing only volatile byproducts. Any organic acid may be used as long as the ester resulting from the reaction has a low vapor pressure such that the ester will evaporate below about 200° C. In this embodiment, an amount of acid (preferably concentrated formic acid) which is about 1 to about 2 times the molar quantity of the alkoxide is added to the solution after adding the water/alcohol mixture. The solution is stirred for a prolonged period of from about 1 hour to about 24 hours, preferably about 12 hours. The reaction proceeds as follows:

$$Zr(OPr)_4 + 2HCOOH \rightarrow ZrO_2 + 2PrOH + 2HCOOPr$$

When formic acid is used, the resulting clusters tend to grow large enough to scatter visible light, thereby giving the stirred solution a milky white appearance. If a smaller average cluster size is desired, then the system may be further acidified to a pH of near 1 by adding a strong acid, such as hydrochloric or nitric acid, in order to partially digest the clusters. The solution is stirred until achieving a desired average cluster size, preferably from about 20 nm to about 100 nm. The cluster size is measured using transmission electron microscopy (TEM), atomic force microscopy (AFM), or simple visual inspection based upon known light scattering phenomena.

Assuming perfect bonding between the particle and matrix, a decrease in particle size at a given volume fraction of particles will increase the elastic constraint on the deforming matrix molecules and lead to an increase in modulus. However, as the particle size approaches molecular dimensions, the very closely spaced crosslinking points of high functionality within the matrix will substantially quench any large scale molecular motions. It is these motions which are important for energy dissipation and fracture toughness.

In order to accommodate both factors, the particles preferably are "nanoparticles," or particles having an average "diameter in nanometers" defined herein as from about 10 nm to about 150 nm, preferably about 50 to about 100 nm. The desired average diameter in nanometers is small enough to provide sufficient transparency for photopolymerization but large enough to provide effective fracture toughness after photopolymerization. In other words, the average diameter in nanometers permits the material to be effectively cured by photopolymerization and also provides effective fracture toughness after curing.

Once the desired average cluster size is achieved through adjustment of the solution pH, the clusters are organofunctionalized with an organofunctional coupling agent. Although irreversible binding is not an absolute necessity, the ideal organofunctional coupling agent readily and irreversibly condenses with reactive groups at the surface of the metal oxide clusters. The organofunctional coupling agent also provides a polymerizable functionality, preferably a double bond functionality, to the clusters to permit the clusters to copolymerize with a suitable surrounding organic matrix resin. The organofunctional coupling agents also preferably render the clusters more hydrophobic.

Suitable organofunctional coupling agents include polymerizable groups, including, but not necessarily limited to photopolymerizable groups such as vinyl, acryl, epoxy, or methacryl groups. Examples include, but are not necessarily limited to mono-, di-, and tri-functional silanes, isocyanates, zirconates, aluminozirconates, zirconyl methacrylate, titanates, and phosphonates. Preferred organofunctional groups, which increase the hydrophobicity of the clusters and also maximize the mechanical strength of the resulting composite are hydrolyzable zirconates having the following general structure:

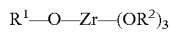

wherein $R^1$ is selected from the group consisting of hydrolyzable alkyl groups having 1 or more carbon atoms and hydrolysable alkenyl groups having 2 or more carbon atoms, said alkyl groups and/or alkenyl groups being effectively eliminatable from the system as free molecules either by volatilization or by isolated copolymerization within the organic matrix resin, and $R^2$ is selected from the group consisting of copolymerizable alkenyl substituents containing 2 or more carbon atoms. $R^1$ generally may be eliminated by volatilization if the number of carbon atoms is less than 9. Preferred organofunctional groups are neopentyl (diallyl) oxy trimethacryl zirconates and neopentyl (diallyl) oxy triacryl zirconates (described in U.S. Pat. No. 4,623,738, incorporated herein by reference).

Aluminozirconates having the following general structure also are preferred as organofunctional groups for zirconia clusters:

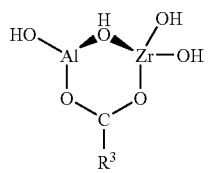

wherein $R^3$ is selected from the group consisting of copolymerizable alkenyl groups and carboxyfunctional substituents containing 1 or more carbon atoms, respectively. Preferred aluminozirconates are methacryloxy aluminozirconates (described in U.S. Pat. Nos. 4,539,049 and 4,539,048, both of which are incorporated herein by reference).

In another preferred embodiment, the polymerizable functionality is reacted with the oxide surface through a phosphonate linkage, which has good hydrolytic stability and will react with the metal-OH bonds only through the ester bonds, as shown below:

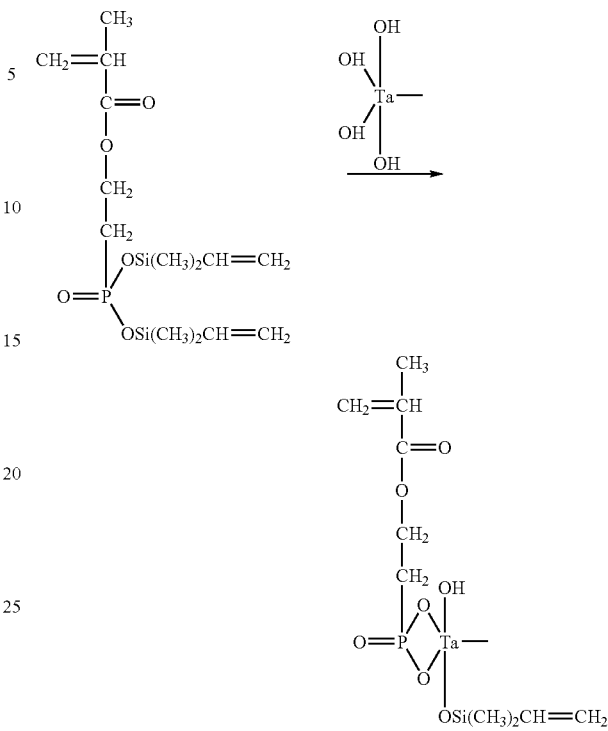

In order to make an especially active phosphonating species, the dimethyl ester of methacryl phosphonate was reacted with a silanating agent to form the hydrolytically unstable vinyl dimethyl silyl ester. The silanating agent can be a chloride, as shown below, or a bromide.

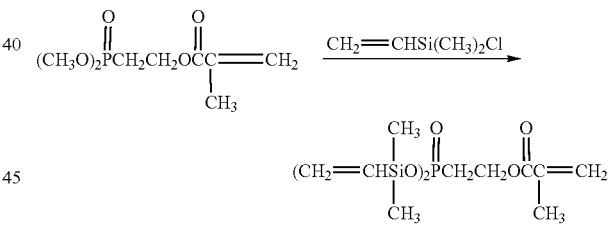

This reaction is quite generic and can be used to form any trialkylsilyl ester (e.g., trimethylsilyl) of any functionalized phosphonate, including vinyl phosphonate. Suitable esters have the general formula:

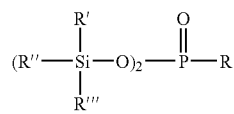

wherein R is a polymerizable group, such as a vinyl, acryl, or methacryl group, and R', R", and R'" are the same or independently selected from the group consisting of alkyl groups and alkenyl groups.

For example, in addition to the trialkyl silyl ester of vinyl phosphonate, phosphonates having the following groups can be used:

1. R is —CH=CH$_2$ and R', R", and R'" each are —CH$_3$ groups;
2. R is

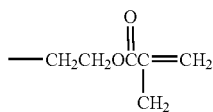

and R', R", and R'" are each —CH$_3$; and
3. R is

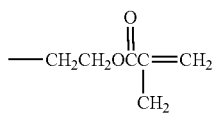

and R', R" and R'" are each —CH$_3$; and
R'" is CH$_2$=CH$_2$

The silyl phosphonate esters can serve two purposes. One purpose is as a surface phosphonating agent, and the other as a surface silanating agent which will generate the hydrophobic surface necessary for incorporation into hydrophobic monomers. If the silane is alkene functionalized, or otherwise functionalized with a polymerizable functionality, then the silane also acts as a coupling agent via the phosphonating agent.

The phosphonating agent may be incorporated into the metal oxide particles using any acceptable means. The phosphonating agent conveniently is incorporated by ester exchange of the metal ethoxide with an acid, such as formic acid. Alternately, the metal oxide prepared using conventional means may be exposed, preferably in an alcohol solution, to the silyl phosphonate and trifunctional silane. Any other suitable incorporation method is acceptable.

Even though a given metal oxide cluster may have experienced extensive phosphonating and silanating, the infrared spectrum still indicates the presence of a substantial amount of surface Ta—OH, the hydroxyls herein referred to as "less reactive groups." The remaining accessible Ta—OH may be further reduced by adding a trifunctional silane, such as 3-(trimethoxysilyl) propyl methacrylate to the formic acid mixture. This component also is useful since the multiple Ta—O—Si bonds formed by the trifunctional silane are more hydrolytically stable than the monofunctional silanes. In addition, the silane effectively blocks access to unreacted Ta—OH bonds. Thus, interparticle hydrogen bonding associations between Ta—OH bonds on adjacent particles is blocked and premature phase separation of a tantalum rich phase in the hydrophobic matrix monomer is avoided.

The required amount of organofunctional coupling agent may vary from about 0.01 to about 0.3 times the molar content of the metal oxide, preferably zirconium oxide, in the ceramer. Quantities on the order of 0.2 times the molar content of zirconium oxide have been used to produce strong ceramers using dimethacrylate resins.

In order to organofunctionalize the clusters, the coupling agents are diluted with an excess of a suitable diluent, preferably an alcohol having from about 1 to about 4 carbon atoms, most preferably propanol, and added to the alcohol-zirconia-cluster solution. It is beneficial to maintain the acidity of the solution at a pH of from about 1 to about 3, preferably at about 3, in order for the reaction between the zirconia clusters and the primary coupling agent to be both timely and effective. The acidity may be maintained by adding a suitable inorganic acid, such as nitric acid. The resulting solution is agitated, preferably by stirring, for a prolonged period of time, preferably at room temperature or ambient temperature, in order to accomplish the organofunctionalization. A typical stirring time is about 3 days.

After the primary organofunctionalization has taken place, during which the "reactive groups" are functionalized, the zirconia clusters may be left in the alcohol solution for further treatment. Alternately, if the solids yield is to be assessed, the clusters may be dried by vacuum evaporation, weighed, and the clusters may be redissolved in one of the lower alcohols, preferably methanol, at a later time. In either case, it is preferable to also functionalize the less reactive groups by forming stable complexes or bonds between the less reactive groups and a secondary, highly mobile adhesion promoter in order to further compatibilize the metal oxide clusters with the relatively hydrophobic resin. The quantity of the "less reactive" hydroxyl groups complexed with the mobile adhesion promoter should be sufficient to displace as many hydroxyl groups from the zirconia surfaces as possible and then to remain in place long enough to allow the particles to be homogeneously dispersed in a highly hydrophobic resin. This typically requires complexation or bonding with about 50% or more of the total quantity of hydroxyl groups.

Preferred "mobile adhesion promoters" are defined as surface-active molecules which strongly bind to the surface of the metal oxide cluster, preferably via primary chemical bonding, most preferably irreversibly. In a preferred embodiment, the polar end of the surface-active molecule preferably is bound to the surface by displacing the hydrogen of a hydroxyl group. The hydrophobic tail of the mobile adhesion promoter may intertwine with, but preferably does not chemically react with molecules in the matrix resin. Suitable mobile adhesion promoters include, but are not necessarily limited to silanes, phosphonates, phosphates, chelating agents, such as acetylacetone, fatty acids, such as stearic acid, fatty alcohols, and ester linked fatty acids. Preferred mobile adhesion promoters are silanating agents.

Preferred silanating agents are silanes bearing substituents selected from the group consisting of: from about 1 to about 3 alkyl groups having from about 1 to about 18 carbon atoms; from about 1 to about 3 alkenyl groups; and, from about 1 to about 3 substituents selected from the group consisting of chlorine, bromine, and an alkoxy group having from about 1 to about 4 carbon atoms. Preferred silanating agents have substituents selected from the group consisting of: one alkenyl group; two alkyl groups having from about 1 to about 3 carbon atoms; and, one alkoxy group having from about 1 to about 3 carbon atoms. A most preferred secondary surface agent is dimethyl ethoxy vinyl silane (DMEOVS) (U.S. Pat. No. 4,504,231, incorporated herein by reference). DMEOVS has the benefit of increasing the double bond density of the cluster surfaces while also being volatile enough that excessive amounts can be easily removed from the system. Nevertheless, the agent's greatest value is its ability to displace as many hydroxyl groups from the zirconia surfaces as possible and then to remain in place long enough to allow the particles to be homogeneously dispersed in a highly hydrophobic resin.

Any existing acid in the system will stabilize the silane against oligomerization and will catalyze its reaction with the cluster surfaces. Therefore, it is preferable to further acidify the solution to a pH of from about 1 to about 2, preferably to about 2, by adding a suitable inorganic acid, such as nitric acid. The resulting solution is again agitated, preferably by stirring at ambient conditions, for a prolonged period of time, typically from about 4 days to about 2 weeks.

Once the secondary coupling agent has been given sufficient time to react with the surface of the metal oxide, preferably at least 4 days, any acid (such as HCl) remaining in the solution may be removed by an acid scavenger. Any insoluble portion (generally less than 10% by weight) is removed by centrifugation, and any free protons in solution (i.e. HCl) is scavenged. Substantially any suitable acid scavenger may be used, such as polyamines and their copolymers. A preferred acid scavenger is polyvinyl pyridine. Using this acid scavenger, the system pH is adjusted upward to at least about 5, but not more than about 6. The supernatant solution is postreacted with a large excess of the secondary surface active agent in order to displace any hydroxyl groups remaining on the particle surfaces If clouding of the solution occurs during postreaction, it may be desirable to centrifuge a second time and postreact again with an excess of the secondary surface active agent.

The functionalized nanoparticles then are ready to be mixed with the matrix monomers. Any transparent monomer comprising functional groups polymerizable with the coupling agent on the metal oxide clusters may be used. Suitable functional groups include, but are not necessarily limited to vinyl, acryl, epoxy, or methacryl groups. For dental applications, methacryl and acryl groups are preferred.

Generally, a solution of from about 10 wt % to about 30 wt % of zirconium oxide nanoparticles in lower alcohol, preferably methanol, is mixed with a solution of a suitable matrix monomers. It is possible that a higher wt % of zirconium oxide nanoparticles also may be used. Suitable matrix monomers include, but are not necessarily limited to glycerol monomethacrylate, glycerol dimethacrylate, hydroxyethylmethacrylate (HEMA), 2,2-bis[p-(2'-hydroxy-3'-methacryloxypropoxy)phenylene]propane ("Bis-GMA), or ethoxylated bis-GMA and various blends of these monomers in combination with known viscosity reducers and photoinitiators or photoactivators. Known viscosity reducers include, but are not necessarily limited to triethyleneglycol dimethacrylate, and polypropylene oxide monomethacrylate. Known photoinitiators and photoactivators include, but are not necessarily limited to camphorquinone and 2-n-butoxyethyl-4-(dimethylamino)benzoate.

Since dimethacrylate resin monomers are soluble in the lower alcohols, it is convenient to add these resins directly to the existing zirconia solution, mixing them thoroughly. This liquid state mixing approach assures that all particles have sufficient opportunity to intimately adhere to the resin monomers. Once the mixture becomes homogeneous, the volatile agents may be directly removed by vacuum evaporation, yielding a single phase composite resin. Alternately, the resulting polymer may be isolated by filtration and/or centrifugation. If a the "complexed fraction" of the hydroxyl groups at the surface of the zirconia clusters is sufficient, the zirconia clusters will not tend to interact with one another or agglomerate, even at near-neutral pH, once incorporated into a hydrophobic resin. Experimental samples contained 10, 20 and 30 wt % nanoparticle loadings.

The hydrophobicity of the nanoparticle can be increased by increasing the complexed fraction, or the number of functionalized Zr—OH bonds. The ability to alter the surface of the nanoparticle in a controlled manner permits control of the working time of the unpolymerized composite and modification of the cured microphase structure of the composite material.

For example, if a hydrophobic, matrix monomer and hydrophilic nanoparticles are dissolved in a common hydrophilic solvent, evaporation of the solvent will yield an initially mobile fluid which rapidly will phase separate to form an elastic gel. Elastic properties are generated by an interpenetrating network phase of hydrophilic metal oxide nanoparticles within the hydrophobic matrix.

If, on the other hand, the hydrophobic matrix monomer and the relatively hydrophobic nanoparticles are mixed in a common solvent and the solvent is evaporated, microphase separation will proceed more slowly providing increased working or storage time in the mobile state.

Generally, the organofunctionalized nanoparticles suspended in an alcohol medium (an "alcosol") are co-dissolved with dental-grade acrylic monomers by addition directly to a flask containing the alcosol suspension. The organofunctionalized nanoparticles dissolve completely in the alcosol. The original alcohol is then evaporated away with the aid of a vacuum pump. The weight of the composite is measured progressively. For a small batch (~5 g), the total evaporation time is approximately 2 hours.

When the weight of the composite no longer changes with continued pumping, the solvent is considered to be sufficiently removed, and the composite is ready to be used, for dental restoration, for stereolithography, etc. In the lab, the composite is used to form specimens, e.g., small molds, and the molds are centrifuged to remove any entrapped air.

Coagulation of the composite is a physically observable phenomenon. Initially upon removal of the solvent, the composite is a "flowable," soft paste, which is easily worked with a spatula. Over time, the paste begins to stiffen. At a definite point in time. herein called the "coagulation point," the material takes on a semi-solid, gelatinous form which is soft, but fractures under pressure. At the coagulation point, the composite no longer flows. If the nanoparticles are sufficiently functionalized, the coagulation point occurs upon the elapse of the following periods of time after removal of the solvent: about 1 minute or more; preferably about 1 hour or more; more preferably about 2 hours or more; and, most preferably about 4 hours or more.

With increased working time, the kinetic development of phase separation can be terminated at different stages by polymerization of the matrix monomer or prepolymer. Interconnectedness of the oxide network can have a strong influence on mechanical, permeability and electrical properties of the material.

By appropriate matching of the surface properties of the nanoparticles and the matrix monomer, it is possible to make a one phase system or generate a very fine phase separation that is insufficient to scatter light to a depth of at least about 1 millimeter, preferably to about 2 millimeters or more. This is of specific importance in many applications because several millimeters in thickness of such a material can be uniformly photocured to a solid. In addition, opacifying particles can be added to the transparent base for control of cosmetic features.

The invention will be better understood with reference to the following examples, which are set forth for purposes of illustration only:

EXAMPLE 1

ZrO$_2$ Cluster Synthesis by Aqueous Hydrolysis

A solution of 10.8367 g of 70% (w/w) zirconium propoxide in propanol was added to a round-bottom flask under nitrogen gas reflux to yield $2.32 \times 10^{-2}$ moles of the pure alkoxide. The solution was diluted by further adding 60 ml normal propanol while stirring with a magnetic stir bar. To completely hydrolyze the alkoxide, the amount of water added was twice the molar amount of zirconium propoxide, i.e. $4.63 \times 10^{-2}$ mole. 0.84 ml water was diluted with 40 ml normal propanol, and this solution was added to the flask dropwise (by burette) while stirring vigorously. The solution gradually became cloudy as the water was added. In order to increase the rate of hydrolysis, the solution was slightly acidified by adding 0.16 ml concentrated nitric acid to the flask. The solution clarified somewhat, remaining slightly hazy. Stirring was continued for about 2 hours. 2.3 ml ($\sim 4.63 \times 10^{-2}$ mol.) of pure neopentyl(diallyl) methacryl zirconate was diluted in 10 ml propanol and the resulting solution was added to the flask dropwise (by pipette), and the solution was stirred for 2 more hours. The system was then further acidified by adding 0.9 ml concentrated nitric acid, resulting in a system pH of about 3. Stirring was continued for about 3 days.

After stirring for 3 days, the flask was evacuated by pumping until only a dry powder remained. The powder was weighed and determined to have a mass near 6.3 g. The powder then was dissolved in methanol with the aid of a vortex mixer until the solids concentration was in the range of 10–20% (w/w). 15.3 ml ($\sim 9.26 \times 10^{-2}$ mol.) of pure dimethyl ethoxy vinyl silane was added to the solution. To prevent polymerization of the silane over time, the solution was further acidified by adding 0.7 ml concentrated nitric acid, resulting in a system pH of about 2. Stirring was continued for one week, and the solution was then neutralized with about 5 g polyvinyl pyridine (2% crosslinked) such that the system pH was greater than 5 but no more than 6. The polymeric base was isolated by filtering the solution.

Once the powder has been solvated, cluster concentration is known and is assumed to remain constant during neutralization. This assumption has been confirmed by re-drying aliquots of the solution. Any and all dilutions preferably are recorded.

EXAMPLE 2

ZrO$_2$ Cluster Synthesis Enhanced by Formic Acid 10.3540 g of 70% (w/w) zirconium propoxide solution was added to a round-bottom flask under nitrogen gas reflux. The solution was diluted with 60 ml normal propanol while stirring with a magnetic stir bar. 0.4 ml water was diluted in 20 ml normal propanol, and this solution was added to the flask dropwise (by burette) while stirring vigorously. The solution became slightly cloudy after the water was added. Stirring was continued for approximately 12 hours, and 1.25 ml concentrated formic acid was added. The resulting solution was stirred for at least 30 minutes, and then 2 ml concentrated hydrochloric acid was added, reducing the system pH to nearly 1. Once the solution was clarified to the point of being only slightly hazy, 2.2 ml of pure neopentyl (diallyl) methacryl zirconate was diluted in 10 ml propanol and added to the flask dropwise (by pipette). Stirring was continued for at least 2 hours, and the solution was pump vacuum dried to a powder.

The resulting powder was dissolved in methanol with the aid of a vortex mixer until the solids concentration was in the range of 10–20% (w/w). 14.6 ml of pure dimethyl ethoxy vinyl silane was added to the solution and the solution was stirred for one week. 4–5 g polyvinyl pyridine (2% crosslinked) was added while monitoring the system pH until it was between 5 and 6. The polymeric base was isolated by centrifugation.

EXAMPLE 3

Composite Formation Using Zirconia Clusters 14.7783 g of a solution having a concentration of clusters of 10.15% (w/w) was added to a round-bottom flask, yielding 1.50 g clusters. Added to this solution, and mixed thoroughly, was 6.00 g of a blend of 37 wt % bis-GMA, 25 wt % tetra ethylene glycol dimethacrylate (TEGDMA), 37.5 wt % bis-EMA (an ethoxylated version of bis-GMA) with 0.2% camphorquinone and 0.3% 2-n-butoxyethyl-4-(dimethylamine)benzoate (CQ/amine) (photoinitiator for on-demand polymerization).

The flask was evacuated after mixing in order to remove the volatile methanol and silane from the system. The yield was 7.50 g of composite resin having a solids content of 20% (w/w). The mechanical properties ($\pm 1$ standard deviation) of a variety of composite specimens prepared as indicated are given in the Table below:

The resin had a fluid consistency which was easily manually packed into transparent silicone molds in order to produce mechanical testing specimens for flexural and fracture toughness testing. Once filled, the specimen molds were centrifuged to aid in the removal of air bubbles prior to photocuring. Specimens were spot cured using a dental curing lamp ($\lambda=470$ nm, QHL 75, Dentsply) for a minimum of one minute at each location. The flexure specimens were 2.5×2.5×25 mm in size while the fracture toughness specimens were 8 mm square and less than 4 mm thick. The geometry and testing approach was taken from the ASTM E399 specification, although the specimen size is somewhat smaller than that recommended. The cured specimens were tested to failure, and the fracture surfaces were analyzed by optical microscopy.

| Mechanical Property | Unfilled Model Resin | 70% Silica-Filled Model Resin | 20% Zirconia Filled Model Resin (Formic Acid Used | 20% Zirconia-Filled Model Resin (Inorganic Acid Used |
|---|---|---|---|---|
| Breaking Stress (psi) | 15271.66 ± 1,695.98 | 18658.58 ± 2,185.93 | 38522.47 ± 1,804.53 | 21816.34 ± 1,995.32 |
| Flexural Modulus (GPa) | 2.36 ± 0.21 | 7.87 ± 0.53 | 15.73 ± 1.93 | 12.80 ± 1.08 |
| Fracture Toughness [ksi(in$^{\frac{1}{2}}$)] | 0.4557 ± 0.0436 | 0.3711 ± 0.2033 | 0.4586 ± 0.0979 | — |

Preliminary TEM images revealed that the average particle size was probably much smaller than the expected ~100 nm value, which was consistent with the high optical transparency of the sample. The average flexural strength of the resins was as much as 251.8 MPa. The elastic modulus of the materials was as much as 15.73 GPa. The fracture toughness did not deteriorate with filler loadings up to 30 wt %.

Many modifications and variations may be made to the embodiments described herein without departing from the spirit of the present invention. The embodiments described herein are illustrative only should not be construed as limiting the scope of the present invention.

We claim:

1. Functionalized zirconium oxide particles comprising:
   surfaces comprising a total quantity of hydroxyl groups comprising a complexed fraction of hydroxyl groups comprising a reactive portion of hydroxyl groups and a less reactive portion of hydroxyl groups;
   said reactive portion of hydroxyl groups being complexed with functionalities selected from the group consisting of functionalities with high steric hindrance, functionalities with low steric hindrance, and a combination thereof;
   said less reactive portion of hydroxyl groups being complexed with said functionalities with low steric hindrance.

2. The functionalized zirconium oxide particles of claim 1 wherein said functionalities having a low steric hindrance comprise mobile adhesion promoters and said functionalities having a high steric hindrance comprise organofunctional coupling agents.

3. The functionalized zirconium oxide particles of claim 2 wherein said complexed fraction of hydroxyl groups is effective to produce a coagulation point of about 1 minute or more.

4. The functionalized zirconium oxide particles of claim 3 wherein said complexed fraction of hydroxyl groups is substantially all of said total quantity of hydroxyl groups.

5. The functionalized zirconium oxide particles of claim 3 wherein a sufficient quantity of said reactive portion of hydroxyl groups is complexed with said organofunctional coupling agent that, upon addition to a resin and curing to form a filled composite, the cured filled composite has a fracture toughness substantially the same as the cured resin alone, upon curing.

6. The functionalized zirconium oxide particles of claim 3 wherein the organofunctional coupling agent comprises a polymerizable group selected from the group consisting of one or more vinyl groups, acryl groups, epoxy groups, and methacryl groups.

7. The functionalized zirconium oxide particles of claim 6 wherein the organofunctional coupling agent comprises a functionality selected from the group consisting of mono-, di-, and tri-functional silanes, isocyanates, zirconates, aluminozirconates, zirconyl methacrylate, titanates, and phosphonates.

8. The functionalized zirconium oxide particles of claim 3 wherein the organofunctional groups are hydrolyzable zirconates having the following general structure:

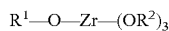

wherein
   $R^1$ is selected from the group consisting of hydrolyzable alkyl groups having 1 or more carbon atoms and hydrolyzable alkenyl groups having 2 or more carbon atoms; and
   $R^2$ is selected from the group consisting of copolymerizable alkenyl substituents containing 2 or more carbon atoms.

9. The functionalized zirconium oxide particles of claim 8 wherein $R^1$ is selected from the group consisting of hydrolyzable alkyl groups having from about 1 to about 9 carbon atoms.

10. The functionalized metal oxide particles of claim 3 wherein the organofunctional coupling agents comprise moieties selected from the group consisting of neopentyl (diallyl) oxy trimethacryl zirconates, neopentyl (diallyl) oxy triacryl zirconates, and aluminozirconates having the following general structure: wherein $R^3$ is selected from the group consisting of copolymerizable alkenyl groups and carboxyfunctional substituents containing 1 or more carbon atoms.

11. The functionalized zirconium oxide particles of claim 3 wherein said organofunctional coupling agents are methacryloxy aluminozirconates.

12. The functionalized zirconium oxide particles of claim 3 wherein one or more of said organofunctional coupling agents and said mobile adhesion promoter is bound to the oxide surface via an ester linkage to a phosphonate group.

13. The functionalized zirconium oxide particles of claim 12 wherein said phosphonate group comprises a silyl ester which may or may not comprise a polymerizable group.

14. The functionalized zirconium oxide particles of claim 3 wherein the mobile adhesion promoter is selected from the group consisting of silanes, phosphonates, phosphates, chelating agents, fatty acids, fatty alcohols, and ester linked fatty acids.

15. The functionalized zirconium oxide particles of claim 3 wherein the mobile adhesion promoter comprises dimethyl ethoxy vinyl silane.

16. The functionalized zirconium oxide particles of claim 3 wherein the organofunctional coupling agents comprise moieties selected from the group consisting of neopentyl (diallyl) oxy trimethacryl zirconates and neopentyl (diallyl) oxy triacryl zirconates.

17. The functionalized zirconium oxide particles of claim 3 wherein said complexed fraction of hydroxyl groups is about 50% or more of said total quantity of hydroxyl groups.

18. The functionalized zirconium oxide particles of claim 2 wherein said complexed fraction of hydroxyl groups is effective to produce a coagulation point of about 1 hour or more.

19. The functionalized zirconium oxide particles of claim 18 wherein said complexed fraction of hydroxyl groups is substantially all of said total quantity of hydroxyl groups.

20. The functionalized zirconium oxide particles of claim 18 wherein a sufficient quantity of said reactive portion of hydroxyl groups is complexed with said organofunctional coupling agent that, upon addition to a resin and curing to form a filled composite, the cured filled composite has a fracture toughness substantially the same as the cured resin alone, upon curing.

21. The functionalized zirconium oxide particles of claim 18 wherein the organofunctional coupling agent comprises a polymerizable group selected from the group consisting of one or more vinyl groups, acryl groups, epoxy groups, and methacryl groups.

22. The functionalized zirconium oxide particles of claim 21 wherein the organofunctional coupling agent comprises a functionality selected from the group consisting of mono-, di-, and tri-functional silanes, isocyanates, zirconates, aluminozirconates, zirconyl methacrylate, titanates, and phosphonates.

23. The functionalized zirconium oxide particles of claim 18 wherein the organofunctional groups are hydrolyzable zirconates having the following general structure:

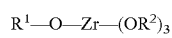

wherein
   $R^1$ is selected from the group consisting of hydrolyzable alkyl groups having 1 or more carbon atoms and hydrolyzable alkenyl groups having 2 or more carbon atoms; and
   $R^2$ is selected from the group consisting of copolymerizable alkenyl substituents containing 2 or more carbon atoms.

24. The functionalized zirconium oxide particles of claim 23 wherein $R^1$ is selected from the group consisting of hydrolyzable alkyl groups having from about 1 to about 9 carbon atoms.

25. The functionalized zirconium oxide particles of claim 18 wherein the organofunctional coupling agents comprise moieties selected from the group consisting of neopentyl (diallyl) oxy trimethacryl zirconates, neopentyl (diallyl) oxy triacryl zirconates, and aluminozirconates having the following general structure:

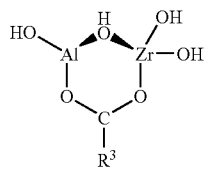

wherein $R^3$ is selected from the group consisting of copolymerizable alkenyl groups and carboxyfunctional substituents containing 1 or more carbon atoms.

26. The functionalized zirconium oxide particles of claim 18 wherein said organofunctional coupling agents are methacryloxy aluminozirconates.

27. The functionalized zirconium oxide particles of claim 18 wherein one or more of said organofunctional coupling agents and said less reactive functionalities is bound to the oxide surface via an ester linkage to a phosphonate group.

28. The functionalized zirconium oxide particles of claim 27 wherein said phosphonate group comprises a silyl ester which may or may not comprise a polymerizable group.

29. The functionalized zirconium oxide particles of claim 18 wherein the mobile adhesion promoter is selected from the group consisting of silanes, phosphonates, phosphates, chelating agents, fatty acids, fatty alcohols, and ester linked fatty acids.

30. The zirconium oxide particles of claim 18 wherein the mobile adhesion promoter comprises dimethyl ethoxy vinyl silane.

31. The functionalized zirconium oxide particles of claim 18 wherein said complexed fraction of hydroxyl groups is about 50% or more of said total quantity of hydroxyl groups.

32. The functionalized zirconium oxide particles of claim 2 wherein said organofunctional coupling agents are irreversibly complexed with said reactive portion of hydroxyl groups.

33. The functionalized zirconium oxide particles of claim 32 wherein the organofunctional coupling agents comprise moieties selected from the group consisting of neopentyl (diallyl) oxy trimethacryl zirconates and neopentyl (diallyl) oxy triacryl zirconates.

34. The functionalized zirconium oxide particles of claim 32 wherein said mobile adhesion promoter comprises dimethyl ethoxy vinyl silane.

35. The functionalized zirconium oxide particles of claim 32 wherein said complexed fraction of hydroxyl groups is about 50% or more of said total quantity of hydroxyl groups.

36. The functionalized zirconium oxide particles of claim 2 wherein said complexed fraction of hydroxyl groups is substantially all of said total quantity of hydroxyl groups.

37. The functionalized zirconium oxide particles of claim 36 wherein said mobile adhesion promoter comprises dimethyl ethoxy vinyl silane.

38. The functionalized zirconium oxide particles of claim 2 wherein a sufficient quantity of said reactive portion of hydroxyl groups is complexed with an organofunctional coupling agent that, upon addition to a resin and curing to form a filled composite, the cured filled composite has a fracture toughness substantially the same as said resin alone, upon curing.

39. The functionalized zirconium oxide particles of claim 2 wherein the organofunctional coupling agent comprises a polymerizable group selected from the group consisting of one or more vinyl groups, acryl groups, epoxy groups, and methacryl groups.

40. The functionalized zirconium oxide particles of claim 39 wherein the organofunctional coupling agent comprises a functionality selected from the group consisting of mono-, di-, and tri-functional silanes, isocyanates, zirconates, aluminozirconates, zirconyl methacrylate, titanates, and phosphonates.

41. The functionalized zirconium oxide particles of claim 2 wherein the organofunctional groups are hydrolyzable zirconates having the following general structure:

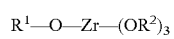

wherein $R^1$ is selected from the group consisting of hydrolyzable alkyl groups having 1 or more carbon atoms and hydrolyzable alkenyl groups having 2 or more carbon atoms; and $R^2$ is selected from the group consisting of copolymerizable alkenyl substituents containing 2 or more carbon atoms.

42. The functionalized zirconium oxide particles of claim 41 wherein $R^1$ is selected from the group consisting of hydrolyzable alkyl groups having from about 1 to about 9 carbon atoms.

43. The functionalized zirconium oxide particles of claim 42 wherein the mobile adhesion promoter is selected from the group consisting of silanes, phosphonates, phosphates, chelating agents, fatty adds, fatty alcohols, and ester linked fatty acids.

44. The functionalized zirconium oxide particles of claim 42 wherein said mobile adhesion promoter comprises dimethyl ethoxy vinyl silane.

45. The functionalized zirconium oxide particles of claim 41 wherein the organofunctional coupling agents comprise moieties selected from the group consisting of neopentyl (diallyl) oxy trimethacryl zirconates and neopentyl (diallyl) oxy triacryl zirconates.

46. The functionalized zirconium oxide particles of claim 45 wherein the mobile adhesion promoter is selected from the group consisting of silanes, phosphonates, phosphates, chelating agents, fatty acids, fatty alcohols, and ester linked fatty acids.

47. The functionalized zirconium oxide particles of claim 45 wherein said mobile adhesion promoter comprises dimethyl ethoxy vinyl silane.

48. The functionalized zirconium oxide particles of claim 41 wherein the mobile adhesion promoter is selected from the group consisting of silanes, phosphonates, phosphates, chelating agents, fatty acids, fatty alcohols, and ester linked fatty acids.

49. The functionalized zirconium oxide particles of claim 41 wherein said mobile adhesion promoter comprises dimethyl ethoxy vinyl silane.

50. The functionalized zirconium oxide particles of claim 2 wherein the organofunctional coupling agents comprise moieties selected from the group consisting of neopentyl (diallyl) oxy trimethacryl zirconates, neopentyl (diallyl) oxy triacryl zirconates, and aluminozirconates having the following general structure:

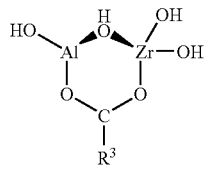

wherein R³ is selected from the group consisting of copolymerizable alkenyl groups and carboxyfunctional substituents containing 1 or more carbon atoms.

51. The functionalized zirconium oxide particles of claim 50 wherein said complexed fraction of hydroxyl groups is about 50% or more of said total quantity of hydroxyl groups.

52. The functionalized zirconium oxide particles of claim 2 wherein said organofunctional coupling agents are methacryloxy aluminozirconates.

53. The functionalized zirconium oxide particles of claim 2 wherein one or more of said organofunctional coupling agent and said mobile adhesion promoter is bound to the oxide surface via an ester linkage to a phosphonate group.

54. The functionalized zirconium oxide particles of claim 53 wherein said phosphonate group comprises a silyl ester which may or may not comprise a polymerizable group.

55. The functionalized zirconium oxide particles of claim 2 wherein the mobile adhesion promoter is selected from the group consisting of silanes, phosphonates, phosphates, chelating agents, fatty acids, fatty alcohols, and ester linked fatty acids.

56. The functionalized zirconium oxide particles of claim 2 wherein the mobile adhesion promoter comprises dimethyl ethoxy vinyl silane.

57. The zirconium oxide particles of claim 2 having an average diameter of from about 10 to about 150 nanometers.

58. The functionalized zirconium oxide particles of claim 2 wherein the organofunctional coupling agents comprise moieties selected from the group consisting of neopentyl (diallyl) oxy trimethacryl zirconates and neopentyl (diallyl) oxy triacryl zirconates.

59. The functionalized zirconium oxide particles of claim 58 wherein said mobile adhesion promoter comprises dimethyl ethoxy vinyl silane.

60. The functionalized zirconium oxide particles of claim 59 wherein said complexed fraction of hydroxyl groups is about 50% or more of said total quantity of hydroxyl groups.

61. The functionalized zirconium oxide particles of claim 2 wherein said complexed fraction of hydroxyl groups is about 50% or more of said total quantity of hydroxyl groups.

62. The functionalized zirconium oxide particles of claim 1 wherein said complexed fraction of hydroxyl groups is effective to produce a coagulation point of about 1 minute or more.

63. The functionalized zirconium oxide particles of claim 62 wherein said complexed fraction of hydroxyl groups is substantially all of said total quantity of hydroxyl groups.

64. The zirconium oxide particles of claim 62 having an average diameter of from about 10 to about 150 nanometers.

65. The functionalized zirconium oxide particles of claim 1 wherein said complexed fraction of hydroxyl groups is effective to produce a coagulation point of about 1 hour or more.

66. The functionalized zirconium oxide particles of claim 65 wherein said complexed fraction of hydroxyl groups is substantially all of said total quantity of hydroxyl groups.

67. The zirconium oxide particles of claim 65 having an average diameter of from about 10 to about 150 nanometers.

68. The functionalized zirconium oxide particles of claim 1 wherein said complexed fraction of hydroxyl groups is about 50% or more of said total quantity of hydroxyl groups.

69. The functionalized zirconium oxide particles of claim 1 wherein said complexed fraction of hydroxyl groups is substantially all of said total quantity of hydroxyl groups.

70. The functionalized zirconium oxide particles of claim 1 wherein the functionality with low steric hindrance is selected from the group consisting of silanes, phosphonates, phosphates, chelating agents, fatty acids, fatty alcohols, and ester linked fatty acids.

71. The zirconium oxide particles of claim 1 having an average diameter of from about 10 to about 150 nanometers.

72. Functionalized zirconium oxide particles comprising a surface comprising a total quantity of hydroxyl groups comprising a complexed fraction of hydroxyl groups and an uncomplexed fraction of hydroxyl groups, said complexed fraction of hydroxyl groups being effective to produce a coagulation point of about one minute or more after removal of a solvent from a mixture of said zirconium oxide particles and a matrix resin.

73. The functionalized zirconium oxide particles of claim 72 wherein said complexed fraction of hydroxyl groups is effective to produce a coagulation point of about one hour or more after removal of a solvent.

74. The functionalized zirconium oxide particles of claim 73 wherein said complexed fraction of hydroxyl groups comprises a less reactive portion of hydroxyl groups complexed with a mobile adhesion promoter and a more reactive portion of hydroxyl groups complexed with an organofunctional coupling agent.

75. The functionalized zirconium oxide particles of claim 74 wherein the organofunctional coupling agent also comprises an adhesion promoter.

76. The functionalized zirconium oxide particles of claim 74 wherein a sufficient quantity of said reactive portion of hydroxyl groups is complexed with said organofunctional coupling agent that, upon addition to a resin and curing to form a filled composite, the cured filled composite has a fracture toughness substantially the same as the cured resin alone, upon curing.

77. The functionalized zirconium oxide particles of claim 74 wherein the organofunctional coupling agent comprises a polymerizable group selected from the group consisting of one or more vinyl groups, acryl groups, epoxy groups, and methacryl groups.

78. The functionalized zirconium oxide particles of claim 77 wherein the organofunctional coupling agent comprises a functionality selected from the group consisting of mono-, di-, and tri-functional silanes, isocyanates, zirconates, aluminozirconates, zirconyl methacrylate, titanates, and phosphonates.

79. The functionalized zirconium oxide particles of claim 74 wherein the organofunctional groups are hydrolyzable zirconates having the following general structure:

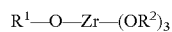

wherein
R¹ is selected from the group consisting of hydrolyzable alkyl groups having 1 or more carbon atoms and hydrolyzable alkenyl groups having 2 or more carbon atoms; and R² is selected from the group consisting of copolymerizable alkenyl substituents containing 2 or more carbon atoms.

80. The functionalized zirconium oxide particles of claim 79 wherein R¹ is selected from the group consisting of hydrolyzable alkyl groups having from about 1 to about 9 carbon atoms.

81. The functionalized zirconium oxide particles of claim 80 wherein the mobile adhesion promoter is selected from the group consisting of silanes, phosphonates, phosphates, chelating agents, fatty acids, fatty alcohols, and ester linked fatty acids.

82. The functionalized zirconium oxide particles of claim 80 wherein said mobile adhesion promoter comprises dimethyl ethoxy vinyl silane.

83. The functionalized zirconium oxide particles of claim 79 wherein the organofunctional coupling agents comprise moieties selected from the group consisting of neopentyl (diallyl) oxy trimethacryl zirconates and neopentyl (diallyl) oxy triacryl zirconates.

84. The functionalized zirconium oxide particles of claim 83 wherein the mobile adhesion promoter is selected from the group consisting of silanes, phosphonates, phosphates, chelating agents, fatty acids, fatty alcohols, and ester linked fatty acids.

85. The functionalized zirconium oxide particles of claim 83 wherein said mobile adhesion promoter comprises dimethyl ethoxy vinyl silane.

86. The functionalized zirconium oxide particles of claim 79 wherein the mobile adhesion promoter is selected from the group consisting of silanes, phosphonates, phosphates, chelating agents, fatty acids, fatty alcohols, and ester linked fatty acids.

87. The functionalized zirconium oxide particles of claim 79 wherein said mobile adhesion promoter comprises dimethyl ethoxy vinyl silane.

88. The functionalized zirconium oxide particles of claim 74 wherein the organofunctional coupling agents comprise moieties selected from the group consisting of neopentyl (diallyl) oxy trimethacryl zirconates, neopentyl (diallyl) oxy triacryl zirconates, and aluminozirconates having the following general structure:

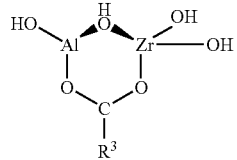

wherein R³ is selected from the group consisting of copolymerizable alkenyl groups and carboxyfunctional substituents containing 1 or more carbon atoms.

89. The functionalized zirconium oxide particles of claim 74 wherein said organofunctional coupling agents are methacryloxy aluminozirconates.

90. The functionalized zirconium oxide particles of claim 74 wherein one or more of said organofunctional coupling agents and said less reactive functionalities is bound to the oxide surface via an ester linkage to a phosphonate group.

91. The functionalized zirconium oxide particles of claim 90 wherein the phosphonate group comprises a silyl ester which may or may not comprise a polymerizable group.

92. The functionalized zirconium oxide particles of claim 74 wherein the mobile adhesion promoter is selected from the group consisting of silanes, phosphonates, phosphates, chelating agents, fatty acids, fatty alcohols, and ester linked fatty acids.

93. The zirconium oxide particles of claim 74 wherein the mobile adhesion promoter comprises dimethyl ethoxy vinyl silane.

94. The functionalized zirconium oxide particles of claim 72 wherein said complexed fraction of hydroxyl groups comprises a less reactive portion of hydroxyl groups complexed with a mobile adhesion promoter and a more reactive portion of hydroxyl groups complexed with an organofunctional coupling agent.

95. The functionalized zirconium oxide particles of claim 94 wherein the organofunctional coupling agent also comprises an adhesion promoter.

96. The functionalized zirconium oxide particles of claim 94 wherein a sufficient quantity of said reactive portion of hydroxyl groups is complexed with said organofunctional coupling agent that, upon addition to a resin and curing to form a filled composite, the cured filled composite has a fracture toughness substantially the same as the cured resin alone, upon curing.

97. The functionalized zirconium oxide particles of claim 94 wherein the organofunctional coupling agent comprises a polymerizable group selected from the group consisting of one or more vinyl groups, acryl groups, epoxy groups, and methacryl groups.

98. The functionalized zirconium oxide particles of claim 97 wherein the organofunctional coupling agent comprises a functionality selected from the group consisting of mono-, di-, and tri-functional silanes, isocyanates, zirconates, aluminozirconates, zirconyl methacrylate, titanates, and phosphonates.

99. The functionalized zirconium oxide particles of claim 94 wherein the organofunctional groups are hydrolyzable zirconates having the following general structure:

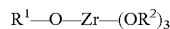

wherein
R¹ is selected from the group consisting of hydrolyzable alkyl groups having 1 or more carbon atoms and hydrolyzable alkenyl groups having 2 or more carbon atoms; and
R² is selected from the group consisting of copolymerizable alkenyl substituents containing 2 or more carbon atoms.

100. The functionalized zirconium oxide particles of claim 99 wherein R¹ is selected from the group consisting of hydrolyzable alkyl groups having from about 1 to about 9 carbon atoms.

101. The functionalized zirconium oxide particles of claim 94 wherein the organofunctional coupling agent comprise moieties selected from the group consisting of neopentyl (diallyl) oxy trimethacryl zirconates, neopentyl (diallyl) oxy triacryl zirconates, and aluminozirconates having the following general structure:

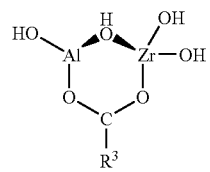

wherein R³ is selected from the group consisting of copolymerizable alkenyl groups and carboxyfunctional substituents containing 1 or more carbon atoms.

102. The functionalized zirconium metal oxide particles of claim 94 wherein said organofunctional coupling agents are methacryloxy aluminozirconates.

103. The functionalized zirconium oxide particles of claim 94 wherein one or more of said organofunctional coupling agents and said less reactive functionalities is bound to the oxide surface via an ester linkage to a phosphonate group.

104. The functionalized zirconium oxide particles of claim 103 wherein the phosphonate group comprises a silyl ester which may or may not comprise a polymerizable group.

105. The functionalized zirconium oxide particles of claim 94 wherein the mobile adhesion promoter is selected from the group consisting of silanes, phosphonates, phosphates, chelating agents, fatty acids, fatty alcohols, and ester linked fatty acids.

106. The zirconium oxide particles of claim 94 wherein the mobile adhesion promoter comprises dimethyl ethoxy vinyl silane.

107. Functionalized zirconium oxide particles comprising:
   surfaces comprising a total quantity of hydroxyl groups comprising a complexed fraction of hydroxyl groups comprising a reactive portion of hydroxyl groups and a less reactive portion of hydroxyl groups;
   said reactive portion of hydroxyl groups being complexed with functionalities selected from the group consisting of functionalities with high steric hindrance, functionalities with low steric hindrance, and a combination thereof;
   said less reactive portion of hydroxyl groups being complexed with said functionalities with low steric hindrance;
   wherein one or more of said functionalities with high steric hindrance and said functionalities with low steric hindrance is bound to the oxide surface via an ester linkage to a phosphonate group.

108. The functionalized zirconium oxide particles of claim 107 wherein said phosphonate group comprises a silyl ester which may or may not comprise a polymerizable group.

* * * * *